United States Patent [19]

Idowu

[11] Patent Number: 5,273,529
[45] Date of Patent: Dec. 28, 1993

[54] GASTROSTOMY TUBE WITH EXPANDABLE INSERTION TIP

[76] Inventor: Olajire Idowu, 1734 Mettler Rd., Lodi, Calif. 95242

[21] Appl. No.: 985,891

[22] Filed: Dec. 4, 1992

[51] Int. Cl.⁵ .................... A61M 31/00; A61M 25/00
[52] U.S. Cl. ........................ 604/49; 604/108; 604/174
[58] Field of Search .............. 604/49, 104–109, 604/167, 169, 174, 175, 178, 256; 606/191, 198

[56] References Cited

U.S. PATENT DOCUMENTS

| | | | |
|---|---|---|---|
| 3,490,457 | 1/1970 | Peterson | 604/105 |
| 4,393,873 | 7/1983 | Nawash et al. | 604/151 |
| 4,543,089 | 9/1985 | Moss | 604/93 |
| 4,555,242 | 11/1985 | Saudagar | 604/96 |
| 4,572,186 | 2/1986 | Gould et al. | 604/104 |
| 4,666,433 | 5/1987 | Parks | 604/178 |
| 4,701,163 | 10/1987 | Parks | 604/178 |
| 4,861,334 | 8/1989 | Nawaz | 604/49 |

OTHER PUBLICATIONS

Gauderer et al "Gastrostomies: Evolution, Techniques, Indications and Complications". *Current Problems In Surgery*. vol. 22, No. 9, Sep. 1986.
Gauderer et al "Feeding Gastrostomy Button: Experience and Recommendations". *Journal of Pediatric Surgery*, vol. 23, No. 1, Jan. 1988, pp. 24–28.
Berman et al Case Report. Journal of Pediatric Gastroenterology and Nutrition, vol. 13, No. 4, 1991, pp. 426–428.
Booklet on Bard Feeding Devices by C. R. Bard, Inc., 1970, 24 pages.

*Primary Examiner*—John D. Yasko
*Assistant Examiner*—Anthony Gutowski
*Attorney, Agent, or Firm*—Robert Charles Hill

[57] ABSTRACT

A gastrostomy tube including a tube with a plurality of flexible legs, each leg having an end joined to an exit end of the tube and another end joined to other ends of the legs to form an expandable Malecot tip. A cord is slideably positioned in each tube with one cord end secured to the joined ends of the legs and another end threaded through the respective leg, through the tube and into a housing located on the entrance end of the tube where it is secured to a capstan. The capstan is secured in a housing attached to the entrance end of the tube. When the capstan is turned, the cords are wrapped around the capstan and pull on the joined ends of the legs so as to cause the legs to buckle and expand laterally, thereby securing the gastrostomy tube in the wall of the abdomen. A one-way valve is located in the tube which permits nutrients to pass from the entrance end, through the tube, and into the stomach but will prevent flow of contents of the stomach in the opposite direction.

9 Claims, 2 Drawing Sheets

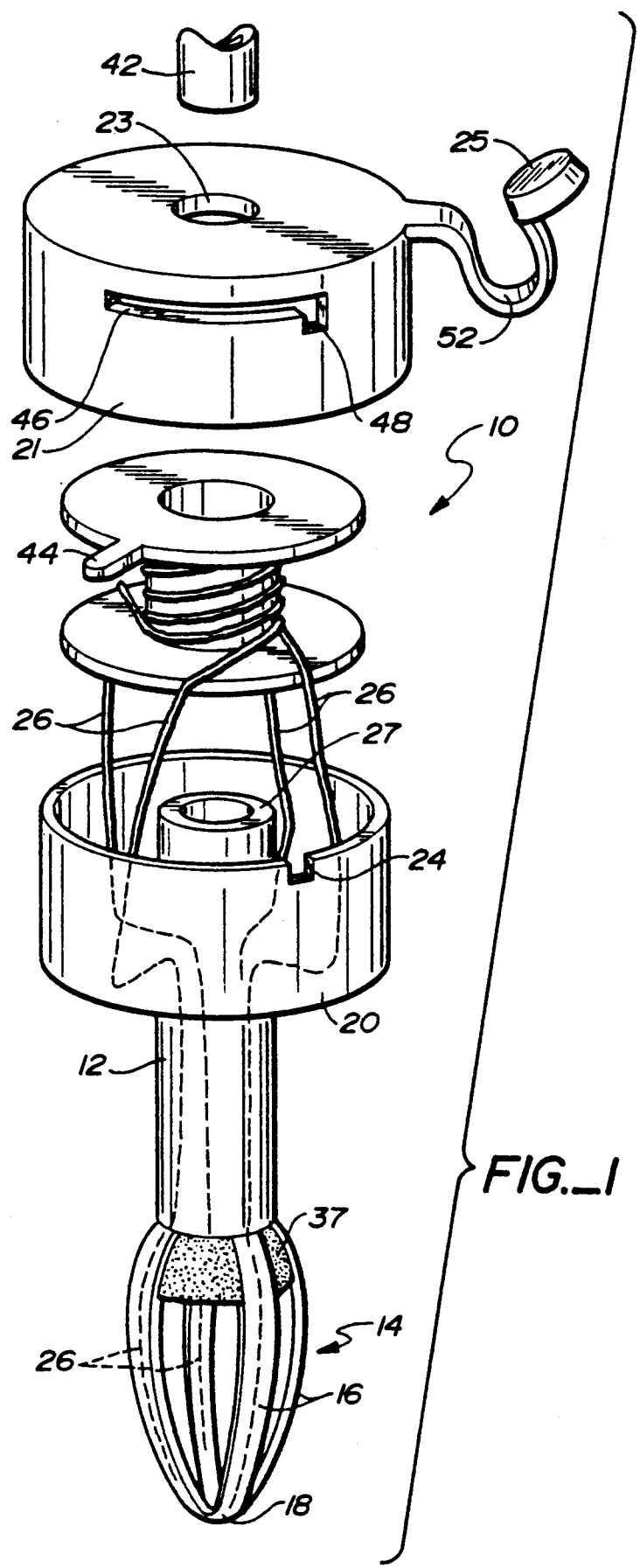
FIG._1

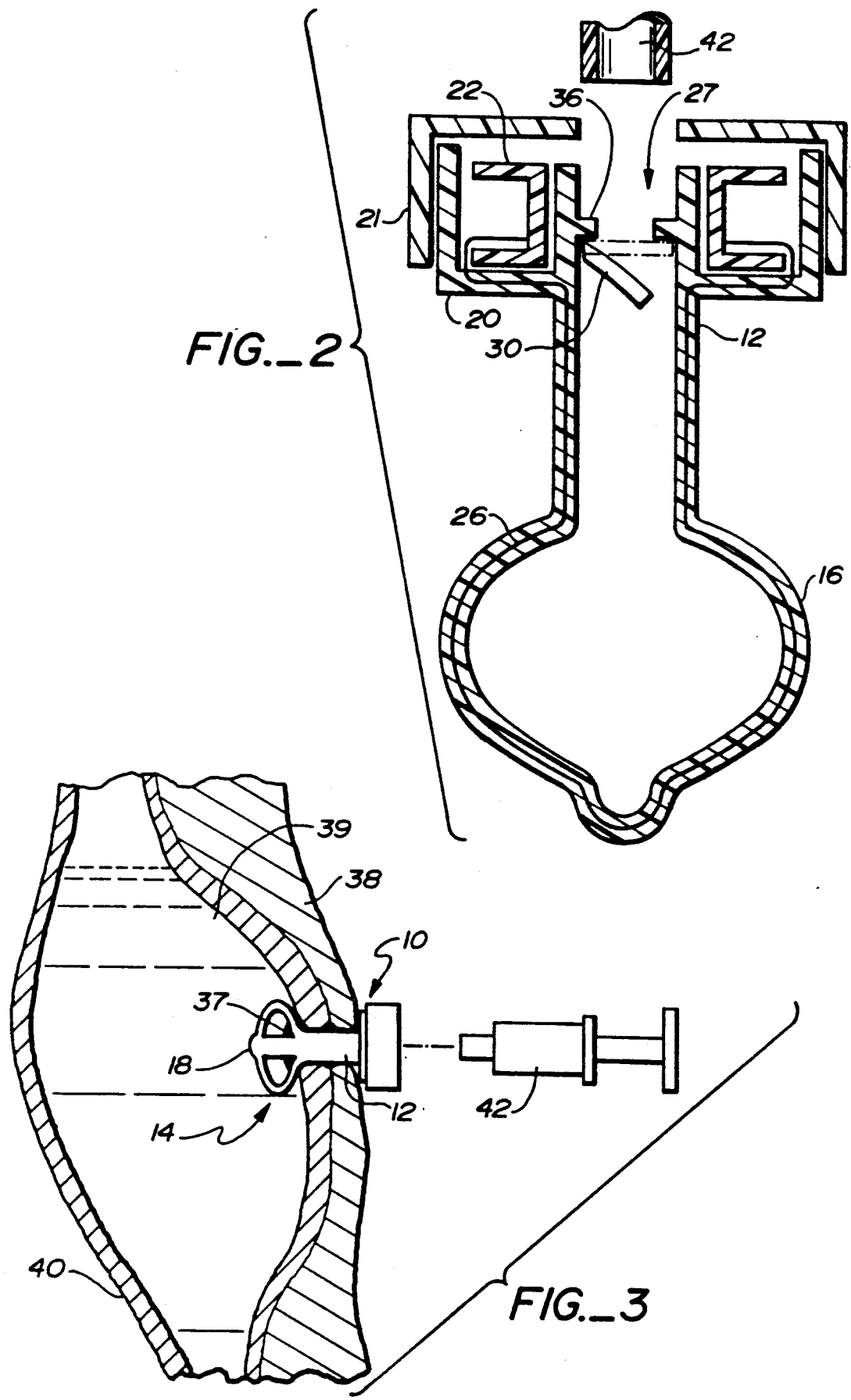

GASTROSTOMY TUBE WITH EXPANDABLE INSERTION TIP

FIELD OF THE INVENTION

This invention relates to improved gastrostomy tubes and other percutaneous tubes and to one-way valves and insertion techniques useful with such tubes.

DESCRIPTION OF THE PRIOR ART

The problem of medical patients unable to feed through the mouth or swallow because of cerebral damage, injury, etc. has been addressed extensively in the literature. (See "Current Problems in Surgery" by M. M. Ravich, vol. XXIII, no. 9, September, 1986, Year Book Medical Publishers, Inc. Chicago and "Feeding Gastrostomy Button" by Michael et al, J. of Pediatric Surgery, v. 23 1988, which are incorporated into this specification as a reference.

A surgical procedure (gastrostomy) for the purpose of feeding has been developed in which a surgical opening is made through the abdominal wall into the stomach. Methods and devices for performing gastrostomy have evolved over a period of more than a hundred years. Improvements have resulted in response to a number of problems associated with the procedure. These problems have included maintaining comfort and convenience for the patient who must endure long periods of having an end of a tube inserted through the abdominal wall into his/her digestive tract through which nourishment is supplied. Another requirement is that the area of the wound be kept clean.

A major problem has been to maintain the tube in the abdominal wall without it being dislodged and drawn into the abdomen by peristaltic action. Tubes have been developed in which the end of the tube is inserted through a relatively small opening in the abdominal wall and then expanded to secure its position. The end of the tube may include an expandable balloon or a Malecott tip for this purpose.

Many types of gastrostomy tubes have been developed but they are characterized by various drawbacks. One shortcoming of the prior art concerns the manner of inserting the gastrostomy tube into the gastrostomy opening.

When the tube is provided with a Malecot (expandable) tip, trained medical personnel insert a metal sylet through the length of the tube and up against a mushroom (Malecot) tip. The surgeon pushes the metal sylet to elongate and straighten the tube as it is pulled through the abdominal wall opening into the stomach. Extremely precise force is needed to elongate the tube for successful placement into the stomach. Caution must be exercised during placement to prevent damage to the abdominal wall and stomach. The removal of replacement of the tube also requires a physician or trained medical personnel to avoid injury to the stomach or abdominal wall.

When the end of the tube is provided with an inflatable balloon, problems with inflation and deflation can develop.

U.S. Pat. No. 4,393,873 to Nawash et al is for a percutaneous transport tube including a tube leading from a fitting connectable to a syringe to an expandable Malecot tip. (A Malecot tip is shown as item 13, FIGS. 1 and 2.) A channel is provided in the wall of the tube through which a stylet is inserted to stretch the Malecot tip during insertion of the tip through the wall of the abdomen. When the tube has been inserted, the stylet is removed so that the Malecot tip expands thereby securing the tube in place. The tube also has a oneway valve that permits passage of nourishment directly into the stomach but prevents liquids from passing out of the stomach through the tube.

U.S. Pat. No. 4,543,089 to Moss is for a gastrointestinal feeding and aspirating device including a tube to be inserted through the abdominal wall. The tube includes a feeding lumen, an aspirating lumen and an inflation lumen. Openings in the tube lead to the three lumens such that, when the tube is inserted through the abdominal wall, the orifice on the end of the feeding lumen opens at a site proximal to the small bowel and is downstream from another orifice which is located at the end of the aspirating lumen. The inflation lumen communicates with a balloon positioned on the tube. After the tube has been put in place, the balloon is inflated with water in order to secure the position of the tube in the abdomen.

U.S. Pat. No. 4,555,242 to Saudagar is an appliance for draining bodily wastes from the bladder of a patient and includes a tube, one end of which is inserted into the bladder, and an inflatable balloon enclosing a substantial portion of the length of the tube. The inserted tip of the tube is bulbous while the remaining length is corrugated.

U.S. Pat. Nos. 4,666,433 to Parks and 4,701,163 to Parks is for a percutaneous gastrointestinal feeding tube including an expandable tip on the inserted end of the tube and a retaining ring that is slideably positioned on the tube to prevent ingestion of the tube into the stomach by peristaltic action. The expandable tip comprises either a balloon or Malecot tip. The balloon is expanded through a one-way valve.

U.S. Pat. No. 4,861,334 to Nawaz is for a gastrostomy tube having a stretchable section of tube between an expandable balloon near a tube end inserted into the stomach and a disk on the exterior supply end of the tube. The tube is initially stretched by a trocar inserted into the tube prior to insertion of the tube into the abdomen. When the tube is in place, the balloon is inflated and the trocar is removed so that the stretchable length of the tube contracts thereby securing the tube in the abdominal wall.

A number of problems remain which are associated with the devices of the prior art.

In devices using expandable balloons to be inflated with gas or water, there is the danger that the balloon or supply passage to the balloon may leak with the result that the tube would be displaced.

In devices having Malecot tips which are contracted by retractable manually operated trocars, there is the danger that the tip of the trocar may be inadvertently extended too far causing damage to the patient. Expansion of the Malecot tip after the tube has been inserted depends on the resilient properties of the silicone plastic. This is not a reliable situation since the resilient properties of plastics (silicone) are variable. It would be advantageous to provide an expandable tip in which expansion is achieved by a positive reproducible force.

SUMMARY OF THE INVENTION

The devices disclosed in all the prior art patents noted above were found lacking for one or more reasons discussed above. Accordingly, it is an object of this invention to provide a gastrostomy tube for positioning in the wall of an abdomen with an entrance end accessible for attachment to a feeding device such as a syringe and an exit end protruding into the stomach. The exit end of the tube is expandable by application of a positive force after the tube is inserted to prevent inadvertent withdrawal of the tube. This is achieved with a Malecot tip that is elongated (unexpanded laterally) in its relaxed state and in condition for insertion through the abdominal wall. The Malecot tip comprises tow or more elongated legs of resilient medium extending away from the end of the tube to a far end where they are joined together. Twine is slideably encapsulated in each leg and extends from the combined ends of the legs back through the legs and tube to a capstan which is rotatably mounted at the supply end of the tube. After the tube has been inserted, the user turns the capstan so as to wind the twine around the capstan. The twine thereby pulls on the joined ends of the legs causing the legs to buckle, expand laterally, and secure the tube in place. The legs have sufficient resilience that the twine is essentially "spring loaded", i.e., if the capstan is turned in the other direction so as to unwind the thread from the capstan, the legs will straighten permitting withdrawal of the gastrostomy tube from the abdomen.

Additional objects and advantages of the invention are made apparent in the following description having reference to the accompanying drawings.

BRIEF DESCRIPTION OF DRAWINGS

FIG. 1 is a perspective exploded view of the gastrosomy tube of this invention showing the Malecot tip contracted.

FIG. 2 is a sectional view of FIG. 1 but showing the Malecot tip expanded.

FIG. 3 is a sectional view of the abdomen with the Gastrosomy tube in place.

DESCRIPTION OF THE BEST MODE

Turning now to a discussion of the drawings, FIG. 1 is an exploded view of the gastrostomy 10 of this invention showing a tube 12 having one end secured to an upper end of a Malecot tip 14. FIG. 2 is a sectional view of FIG. 1. The Malecot tip 14 includes four separate flexible legs 16, all joined at the lower end 18. The upper end of the tube is expanded to a housing 20 which houses a capstan 22. A cap 21 fits over the housing 20. The capstan is rotatably mounted on an upper length 24 of tube 12. Four cords 26 are shown as dotted lines. One cord 26 is slideably enclosed in one leg 16 respectively and leads from end 18, through the respective leg 16, through tube 12, into the housing 20, and is secured to the capstan 22.

FIGS. 1 and 2 show a one way valve 30 (flap) which opens to permit passage of nutrients from the entry end 37 to the exit end 14 of the tube 12. As shown in phantom in FIG. 2, the valve 30 closes on seat 36 if pressure in the stomach forces bodily fluid or gas in the reverse direction.

FIGS. 1 and 3 show a flat thin sheath 37 extending from the base of one leg 16 to another leg. This thin sheath spreads out like an umbrella when the capstan is rotated to buckle the legs. This thin sheath will prevent leakage of bodily fluids 39 that might otherwise occur from intra abdominal pressure when the patient coughs or cries.

FIG. 3 shows the gastrostomy tube 10 positioned in the wall 38 of the abdomen with one end 18 inserted into the stomach 40. A syringe 42 is poised for injecting nutrients through the tube 12. A hole 23 in cap 21 accommodates mating of the syringe to the entrance end 24 of tube 12. After insertion of the tube 12 into the abdomen, the detent 44 (FIG. 1), protruding through slot 46, is turned to engage notch 48 thereby rotating capstan 22 so as to wind cords 26 around the capstan 22 and pull on end 18 causing legs 16 to buckle as shown in FIGS. 2 and 3. The tube is thereby prevented from being drawn into the stomach nor can the tube be withdrawn by virtue of the expanded Malecot tip 14.

A tab 52 has one end attached to cap 21 with a plug 25 on the other end that may be inserted into the open entrance end 27 when the feeding device 42 is detached.

The method of using this invention for injecting nutrients through the abdomen directly into the stomach includes the steps of incising an opening in the abdominal wall, inserting the tip of the gastrostomy tube of this invention through the incised abdominal wall into the stomach, attaching a feeding device to the entrance end of the tube, injecting nutrients through the tube from the entrance end into the stomach, removing the feeding device, turning the capstan thereby expanding the Malecot tip and placing a plug into the entrance end.

Other modifications could be made within the scope of the invention which is accordingly defined only by the following claims which are further exemplary of the invention.

What is claimed is:

1. A gastrostomy tube for injecting nutrients from a feeding device directly into a stomach of a user, said gastrosomy tube comprising:
   a tube having an open entrance end and an open exit end;
   a plurality of flexible legs, each leg having a first end joined to said other first ends of said legs and a second end joined to said exit end of said tube;
   a capstan rotatably mounted on said entrance end of said tube;
   a plurality of cords, each cord slideably enclosed within one of said legs respectively, each cord having one end secured to said first end of said respective leg and extending through said respective leg and through said tube and having another end of said cord attached to said capstan such that, when said capstan is rotated, said cords will wrap around said capstan and buckle said legs.

2. A gastrostomy tube as in claim 1 which comprises a housing means, substantially cylindrical for enclosing said capstan, secured adjacent to said entrance end of said tube.

3. A gastrostomy tube as in claim 2 wherein a length of said tube extends inside said housing such that said capstan is rotateably mounted on said length and said entrance end of said tube is accessible to said feeding device.

4. A gastrostomy tube as in claim 1 further comprising a syringe connected to said entrance end.

5. A gastrostomy tube as in claim 2 which comprises:
   a cap mounted on said housing with a hole such as to permit attachment of said feeding device to said entrance tube end of said tube;
   said cap having a surface with a slot and a notch;
   said capstan having a detent protruding through said slot and arranged in operable combination with said slot and notch to permit turning said capstan when said detent is slid in said slot and securing said capstan by securing said detent in said notch.

6. A gastrostomy tube as in claim 5 which comprises a tab having one end secured to said cap and another end with a plug means for detachable engagement in said open entrance end.

7. A gastrostomy tube as in claim 1 which comprises a valve flap and seat positioned at said entrance end of said tube, said valve flap, seat and tube arranged in operable combination with one another to permit said valve flap to be opened when food is sent from said entrance end to said exit end of said tube and closed to prevent body fluids from escaping through said tube from said exit end to said entrance end.

8. A gastrostomy tube as in claim 1 which comprises a sheath means attached to the base of the legs for preventing leakage of bodily fluids.

9. A method for injecting nutrients through a wall of an abdomen directly into the stomach which includes the steps;

incising an opening in said abdominal wall;

inserting an exit end of a gastrostomy tube through said incised abdominal wall into said stomach wherein said gastrostomy tube comprises a tube having a Malecot tip on said exit end with ends of cords secured to a distal end of said Malecot tip, said cords leading through said tube and secured to a capstan rotatably mounted on an entrance end of said tube outside said abdominal wall;

attaching a feeding device to said entrance end of said tube;

injecting nutrients through said tube from said entrance end to said exit end and into said stomach;

removing said feeding device from said entrance end;

turning said capstan thereby expanding said Malecot tip; and placing a plug into said entrance end.

* * * * *